(12) United States Patent
Mandwal (10) Patent No.: US 11,937,984 B2
(45) Date of Patent: Mar. 26, 2024

(54) ACTIVE INGRESS DETECTION SYSTEM FOR MEDICAL PROBES

(71) Applicant: GE Precision Healthcare LLC, Wauwatosa, WI (US)

(72) Inventor: Rajeev C. Mandwal, Linz (AT)

(73) Assignee: GE Precision Healthcare LLC, Wauwatosa, WI (US)

( * ) Notice: Subject to any disclaimer, the term of this patent is extended or adjusted under 35 U.S.C. 154(b) by 670 days.

(21) Appl. No.: 17/002,435

(22) Filed: Aug. 25, 2020

(65) Prior Publication Data

US 2022/0061820 A1    Mar. 3, 2022

(51) Int. Cl.
*A61B 8/00*  (2006.01)
*G01L 19/00*  (2006.01)
*G01N 33/00*  (2006.01)
*G01S 7/52*  (2006.01)
*G01S 15/89*  (2006.01)
(Continued)

(52) U.S. Cl.
CPC ............ *A61B 8/546* (2013.01); *A61B 8/4472* (2013.01); *A61B 8/4488* (2013.01); *A61B 8/4494* (2013.01); *A61B 8/461* (2013.01); *G01L 19/0092* (2013.01); *G01N 33/0036* (2013.01); *G01S 7/52053* (2013.01); *G01S 15/8934* (2013.01); *G05B 23/0218* (2013.01); *G16H 40/67* (2018.01)

(58) Field of Classification Search
CPC ............ G01L 19/0092; G01N 33/0036; G05B 23/0218; G16H 40/40; G16H 40/67; A61B 8/4444; A61B 8/4472; A61B 8/4488; A61B 8/4494; A61B 8/461; A61B 8/54; A61B 8/546; A61B 8/58
See application file for complete search history.

(56) References Cited

U.S. PATENT DOCUMENTS 5,402,769 A    4/1995  Tsuji
5,868,664 A *  2/1999  Speier ................... A61B 1/042
                                                  600/134
(Continued)

FOREIGN PATENT DOCUMENTS

CN    104545989 A    4/2015
CN    106999149 B    9/2020

OTHER PUBLICATIONS

CN application 202110926196.7 filed Aug. 12, 2021—Office Action dated Jun. 28, 2023; 19 pages.
(Continued)

*Primary Examiner* — Kristina M Deherrera
*Assistant Examiner* — Gedeon M Kidanu (57) ABSTRACT

The present disclosure relates to a system and method for actively detecting an ingress of a medical probe. In accordance with certain embodiments, a method includes monitoring, with a sensor within a medical probe, an internal environment of the medical probe, detecting, with the sensor, at least one of a temperature, pressure, humidity, or concentration of a gas within the medical probe, determining, with a processor that is in communication with the sensor, whether a seal that hermetically seals the medical probe has failed as a function of at least one of the temperature, pressure, humidity, or concentration of the gas, and outputting, with the processor, a notification that indicates whether the seal has failed.

9 Claims, 4 Drawing Sheets

(51) Int. Cl.
 *G05B 23/02* (2006.01)
 *G16H 40/67* (2018.01)

(56) References Cited

U.S. PATENT DOCUMENTS

| | | | | |
|---|---|---|---|---|
| 6,004,273 | A * | 12/1999 | Sakamoto | A61B 8/12 600/459 |
| 6,126,606 | A * | 10/2000 | Bergstoel | A61B 8/12 600/459 |
| 2011/0156922 | A1* | 6/2011 | Chen | A61B 8/00 340/679 |
| 2011/0190579 | A1* | 8/2011 | Ziarno | A61B 1/00096 600/109 |
| 2020/0229682 | A1* | 7/2020 | Iikura | A61B 1/00057 |
| 2020/0268351 | A1* | 8/2020 | Chiang | G01S 7/52082 |
| 2022/0000375 | A1* | 1/2022 | Meisal | A61B 7/003 |
| 2022/0015744 | A1* | 1/2022 | Valentin | A61B 8/4444 |

OTHER PUBLICATIONS

CN104545989 English Abstract; Espacenet.com search results Sep. 28, 2023; 1 page.
CN106999149 English Abstract; Espacenet.com search results Sep. 28, 2023; 1 page.

* cited by examiner

ACTIVE INGRESS DETECTION SYSTEM FOR MEDICAL PROBES

TECHNICAL FIELD

This disclosure relates to an active ingress detection system for a medical probe, and more particularly, to a failed seal detection system for an ultrasound probe.

BACKGROUND

Reusable medical probes (i.e., ultrasound probes, thermometers, endoscopes, etc.) often contain electronics within them. Reusable medical probes may be cleaned between use and are sealed in order to prevent the ingress of water and other chemicals that may harm the contained electronics during a cleaning. Unfortunately, repeated use and washings may cause a seal that hermetically seals the probe to degrade. Seal degradation may allow water and chemicals from a sanitizing solution to enter the probe and harm electronics stored therein. As a result, a reusable medical probe may malfunction or fail completely. Therefore, it is necessary to detect when a seal of a medical has failed.

SUMMARY

In one embodiment, the present disclosure provides a method. The method comprises monitoring, with a sensor within a medical probe, an internal environment of the medical probe, detecting, with the sensor, at least one of a temperature, pressure, humidity, or concentration of a gas within the medical probe, determining, with a processor that is in communication with the sensor, whether a seal that hermetically seals the medical probe has failed as a function of at least one of the temperature, pressure, humidity, or concentration of the gas, and outputting, with the processor, a notification that indicates whether the seal has failed.

In another embodiment, the present disclosure provides system. The system comprises a medical probe, a sensor within the medical probe, a processor in communication with the sensor, and a computer readable storage medium in communication with the processor, wherein the processor executes program instructions stored in the computer readable storage medium which cause the processor to: receive at least one of a temperature, pressure, humidity, or concentration of a gas from the sensor, determine whether at least one of the temperature, pressure, humidity, or concentration of a gas is above or below a threshold, generate a notification in response to determining whether one at least one of the temperature, pressure, humidity, or concentration of the gas is above or below the threshold, and output the notification.

In yet another embodiment, the present disclosure provides an ultrasound probe. The ultrasound probe comprises a first transducer array, a housing, and a sensor within the housing and configured to detect at least one of a temperature, pressure, humidity, or concentration of a gas within the housing for the purpose of determining a seal of the ultrasound probe has failed.

BRIEF DESCRIPTION OF THE DRAWINGS

Various aspects of this disclosure may be better understood upon reading the following detailed description upon reference to the drawings in which.

The drawings illustrate specific aspects of the described components, systems, and methods for actively detecting an ingress of a medical probe. Together with the following description, the drawings demonstrate and explain the principles of the structures, methods, and principles described herein. In the drawings, the thickness and size of components may be exaggerated or otherwise modified for clarity. Well-known structures, materials, or operations are not shown or described in detail to avoid obscuring aspects of the described components, systems, and methods.

DETAILED DESCRIPTION

One or more specific embodiments of the present disclosure are described below in order to provide a thorough understanding. These described embodiments are only examples of systems and methods for actively detecting an ingress of a medical probe. The skilled artisan will understand that specific details described in the embodiments can be modified when being placed into practice without deviating from the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (i.e., a material, element, structure, number, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

While in use, medical probes produce heat that causes temperature and pressure within the probe to rise. When properly sealed, the temperature and pressure within the probe is predictable. When the seal fails, heat may escape the probe causing the temperature and pressure within the probe to deviate from a predicted temperature and pressure. Providing a system and/or a method that determines when the temperature and/or pressure within a medical probe falls below a threshold aids in determining that a seal that hermetically seals the probe has failed. The threshold may be determined as a function of a time a medical probe is on as the longer the medical probe is on, the more heat the probe generates. When properly sealed, the rise in temperature (and therefore pressure) is a generally linear function. Some embodiments of the present disclosure provide a system and/or method that determines when temperature and/or pressure within a medical probe falls below a threshold.

Furthermore, when the seal fails water and/or other chemicals associated with sanitizing solutions may enter the probe and the heat generated by the probe may cause the water and/or the chemicals to evaporate within the probe. Providing a system that determines when the microenvironment within the probe becomes humid and/or includes gases associated cleaning solutions aids in determining that a seal that hermetically seals the probe has failed. Some embodiments of the present disclosure provide a system and/or a method that determines when the microenvironment within the probe becomes humid and/or includes gases associated with cleaning solutions.

Figure 1:
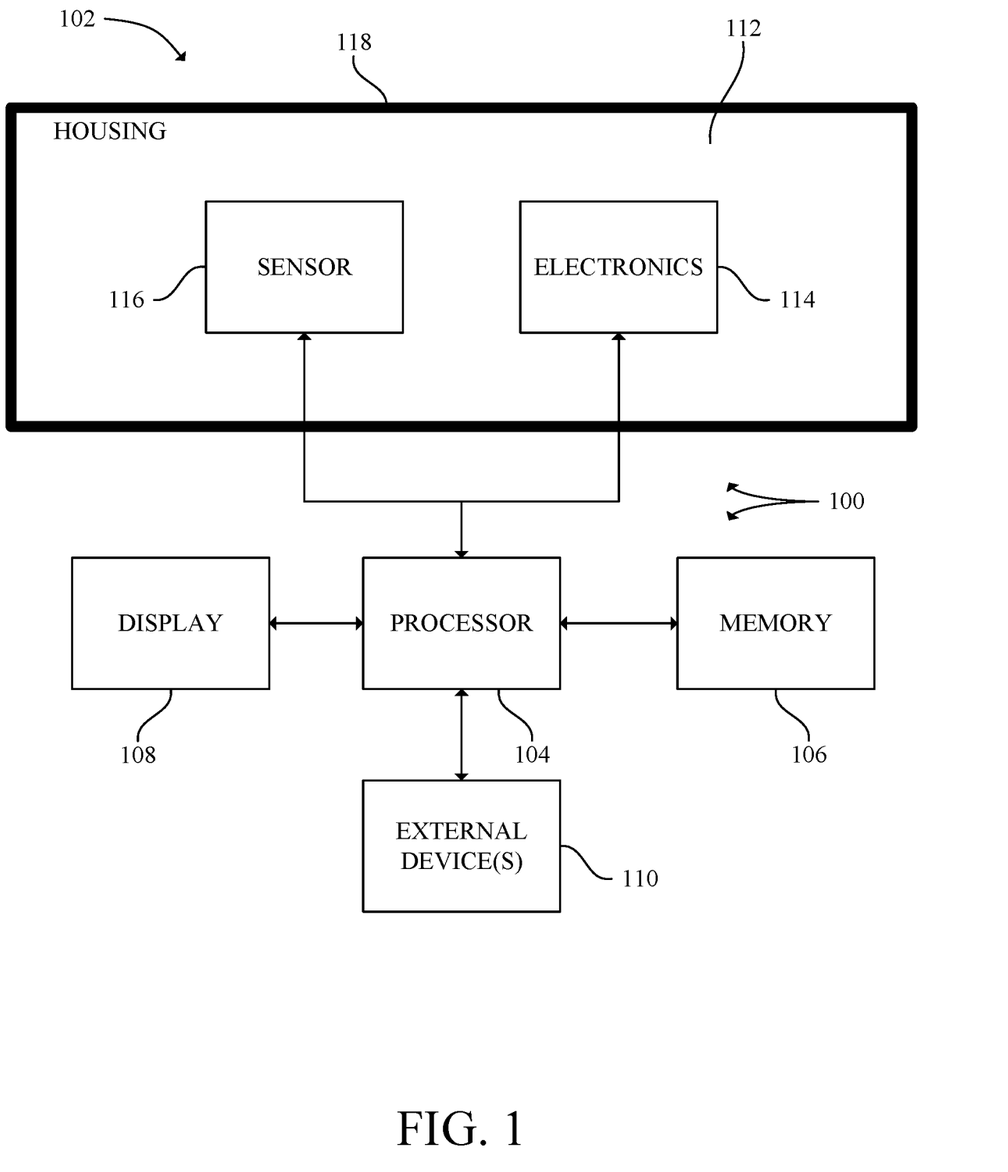
FIG. 1 is a schematic diagram of a medical probe system in accordance with an exemplary embodiment.

Referring now to FIG. 1, a medical probe system 100 is shown in accordance with an exemplary embodiment. As illustrated in FIG. 1, in some embodiments, the medical probe system 100 includes a medical probe 102, a processor 104, system memory 106, a display 108, and one or more external devices 110. The medical probe 102 may be any medical probe capable of capturing data from a patient including (i.e., ultrasound probe, thermometer, endoscope, etc.). The medical probe 102 includes a housing 112, electronics 114, a sensor 116, and a seal 118.

The housing 112 contains the electronics 114 and the sensor 116. The electronics 114 include electronics for operating the medical probe 102. For example, when the medical probe 102 is a thermometer, the electronics 114 may include electronics for detecting a body temperature of a patient. The electronics 114 are in communication with the processor 104 via a wired and/or a wireless connection thereby allowing the electronics 114 to receive data from/send data to the processor 104. In one embodiment, the electronics 114 may connect the medical probe 102 to a network (i.e., a wide area network (WAN), a local area network (LAN), a public network (the Internet), etc.) which allows the medical probe 102 to transmit data to and/or receive data from the processor 104 when the processor 104 is connected to the same network. In another embodiment, the electronics 114 directly connect the medical probe 102 to the processor 104 thereby allowing the medical probe 102 to transmit data directly to and receive data directly from the processor 104.

The sensor 116 monitors the internal environment of the housing 112 and detects at least one of a temperature, pressure, humidity or concentration of a gas within the housing 112. The gas may include a gas that is generated when a cleaning solution evaporates within the housing 112. The gases include, but are not limited to, ethane, isoprene, ethanol, acetone, and carbon monoxide. The sensor 116 is in communication with the processor 104 via a wired and/or a wireless connection thereby allowing the sensor 116 to receive data from/send data to the processor 104. Specifically, the sensor 116 sends a signal indicative of at least one of the detected temperature, pressure, humidity or concentration of a gas to the processor 104.

The seal 118 seals the housing 112 such that water and/or other chemicals do not enter the housing 112 and harm the electronics 114 and the sensor 116. In some embodiments, the seal 118 is an ingress protection (IP) rated seal. For example, the seal 118 may be an IPX7 rated seal which prevents water ingress at a depth of up to a meter for 30 minutes. In other embodiments, the seal 118 provides an airtight (hermetic) seal.

The processor 104 may be a processor of a computer system. A computer system may be any device/system that is capable of processing and transmitting data (i.e., tablet, handheld computing device, smart phone, personal computer, laptop, network computer, etc.). The processor 104 is in communication with the system memory 106. In one embodiment, the processor 104 may include a central processing unit (CPU). In another embodiment, the processor 104 may include other electronic components capable of executing computer readable program instructions, such as a digital signal processor, a field-programmable gate array (FPGA), or a graphics board. In yet another embodiment, the processor 104 may be configured as a graphical processing unit with parallel processing capabilities. In yet another embodiment, the processor 104 may include multiple electronic components capable of carrying out computer readable instructions. For example, the processor 104 may include two or more electronic components selected from a list of electronic components including: a CPU, a digital signal processor, an FPGA, and a graphics board.

The system memory 106 is a computer readable storage medium. As used herein a computer readable storage medium is any device that stores computer readable program instructions for execution by a processor and is not construed as being transitory per se. Computer readable program instructions include programs, logic, data structures, modules, architecture etc. that when executed by a processor create a means for implementing functions/acts. Computer readable program instructions when stored in a computer readable storage medium and executed by a processor direct a computer system and/or another device to function in a particular manner such that a computer readable storage medium comprises an article of manufacture. System memory as used herein includes volatile memory (i.e., random access memory (RAM) and dynamic RAM (DRAM)) and nonvolatile memory (i.e., flash memory, read-only memory (ROM), magnetic computer storage devices, etc.). In some embodiments, the system memory 106 may further include cache.

The display 108 and the one or more external devices 110 are connected to and in communication with the processor 104 via an input/output (I/O) interface. The one or more external devices 110 include devices that allow a user to interact with/operate the medical probe 102 and/or a computer system with the processor 104. As used herein, external devices include, but are not limited to, a mouse, keyboard, and a touch screen.

The display 108 displays a graphical user interface (GUI). As used herein, a GUI includes editable data (i.e., patient data) and/or selectable icons. A user may use an external device to select an icon and/or edit the data. Selecting an icon causes a processor to execute computer readable program instructions stored in a computer readable storage medium which cause a processor to perform various tasks. For example, a user may use an external device 110 to select an icon which causes the processor 104 to control medical probe 102.

Figure 2:
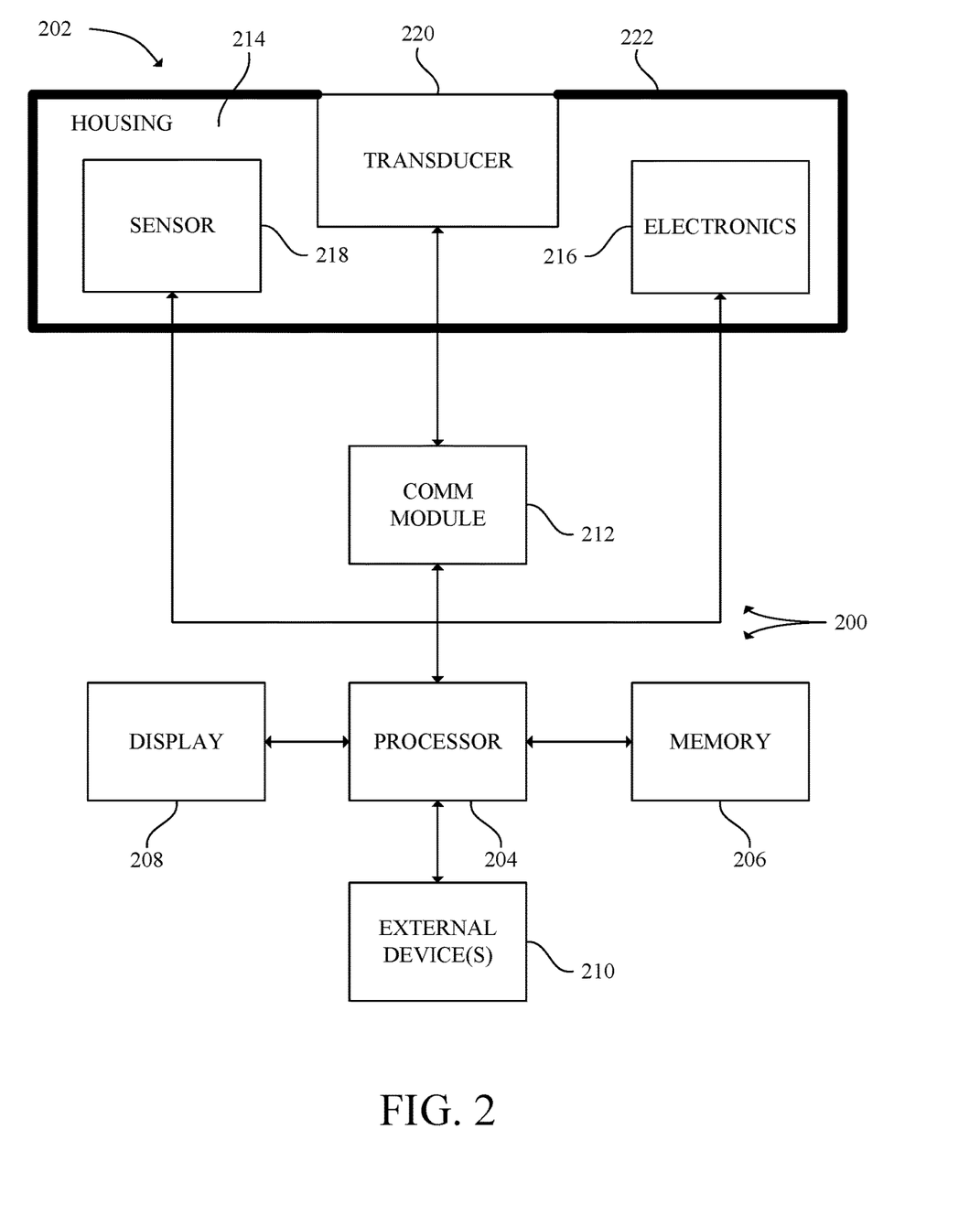
FIG. 2 is a schematic diagram of an ultrasound system in accordance with an exemplary embodiment.

Referring now to FIG. 2, an ultrasound system 200 is shown in accordance with an exemplary embodiment. The ultrasound system 200 is an embodiment of the medical probe system 100. As illustrated in FIG. 2, in some embodiments, the ultrasound system 200 includes an ultrasound probe 202, a processor 204, a system memory 206, a display 208, one or more external devices 210, and a communication module 212.

The processor 204 may be a processor of a computer system and is in communication with the system memory 206. In one embodiment, the processor 204 may include a CPU. In another embodiment, the processor 204 may include other electronic components capable of executing computer readable program instructions. In yet another embodiment, the processor 204 may be configured as a graphical processing unit with parallel processing capabilities. In yet another embodiment, the processor 204 may include multiple electronic components capable of carrying out computer readable instructions. The system memory 206 is a computer readable storage medium.

The display 208 and the one or more external devices 210 are connected to and in communication with the processor 204 via an input/output (I/O) interface. The one or more external devices 210 allow a user to interact with/operate the ultrasound probe 202 and/or a computer system with the processor 204.

The ultrasound probe 202 includes a housing 214, electronics 216, a sensor 218, a transducer array 220, and a seal 222. The housing 214 contains the electronics 216, the sensor 218, and at least a portion of the transducer array 220. The electronics 216 include electronics for operating the ultrasound probe 202 and are in communication with the processor 204 via a wired and/or a wireless connection thereby allowing the electronics 216 to receive data from/send data to the processor 204. In one embodiment, the electronics 216 may connect the ultrasound probe 202 to a network which allows the ultrasound probe 202 to transmit data to and/or receive data from the processor 204 when the processor 204 is connected to the same network. In another embodiment, the electronics 216 directly connect the ultrasound probe 202 to the processor 204 thereby allowing the ultrasound probe 202 to transmit data directly to and receive data directly from the processor 204.

The sensor 218 monitors the internal environment of the housing 214 and detects at least one of a temperature, pressure, humidity or concentration of a gas within the housing 214. The gas may include a gas that is generated when a cleaning solution evaporates within the housing 214. The gases include, but are not limited to, ethane, isoprene, ethanol, acetone, and carbon monoxide. The sensor 218 is in communication with the processor 204 via a wired and/or a wireless connection thereby allowing the sensor 218 to receive data from/send data to the processor 204. Specifically, the sensor 218 sends a signal indicative of at least one of the detected temperature, pressure, humidity or concentration of a gas to the processor 204.

The seal 222 seals the housing 214 such that water and/or other chemicals do not enter the housing 214 and harm the electronics 216, the sensor 218, and the transducer array 220. In some embodiments, the seal 222 is an ingress protection (IP) rated seal. In other embodiments, the seal 222 provides an airtight (hermetic) seal.

The transducer array 220 includes, in some embodiments, an array of elements that emit and capture ultrasonic signals. In one embodiment the elements may be arranged in a single dimension (a "one-dimensional-transducer array"). In another embodiment the elements may be arranged two dimensions (a "two-dimensional transducer array"). Furthermore, the transducer array 220 may be a linear array, a curved array, a phased array, a linear phased array, a curved phased array, etc. The transducer array 220 may be a 1D transducer array, a 1.25D transducer array, a 1.5D transducer array, a 1.75D transducer array, or a 2D array according to various embodiments. The transducer array 220 may be in a mechanical 3D or 4D ultrasound probe 202 that is configured to mechanically sweep or rotate the transducer array 220 with respect to the ultrasound probe 202. Instead of an array of elements, in other embodiments the transducer array 220 may have a single transducer element.

Figure 3:
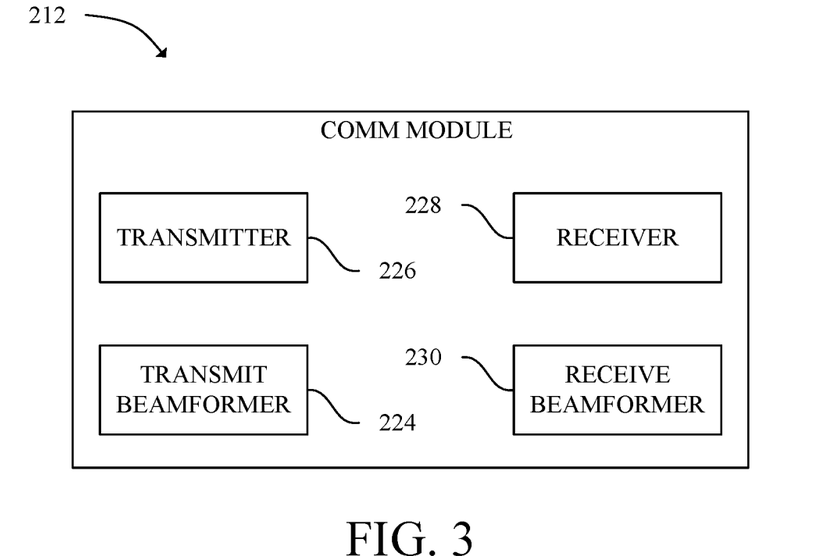
FIG. 3 is a is a schematic diagram a communication module in accordance with an exemplary embodiment.

While FIG. 2 depicts the ultrasound probe 202 as including one transducer array 220, in some embodiments, as depicted in FIG. 3, the ultrasound probe 202 includes a first transducer array 220A and a second transducer array 220B thereby defining a dual array ultrasound probe. The first transducer array 220A and the second transducer array 220B may include a single element, may be a one-dimensional array, a two-dimensional array, a 1.25D array, a 1.5D array, a 1.75D array, or a 2D array. Furthermore, the first transducer array 220A and the second transducer array 220B may be a linear array, a curved array, a phased array, a linear phased array, a curved phased array, etc.

The transducer array 220 is in communication with the communication module 212. The communication module 212 connects the ultrasound probe 202 to the processor 204 via a wired and/or a wireless connection. The processor 204 may execute computer readable program instructions stored in the system memory 206 which may cause the transducer array 220 to acquire ultrasound data, activate a subset of elements, and a emit an ultrasonic beam in a particular shape.

Figure 4:
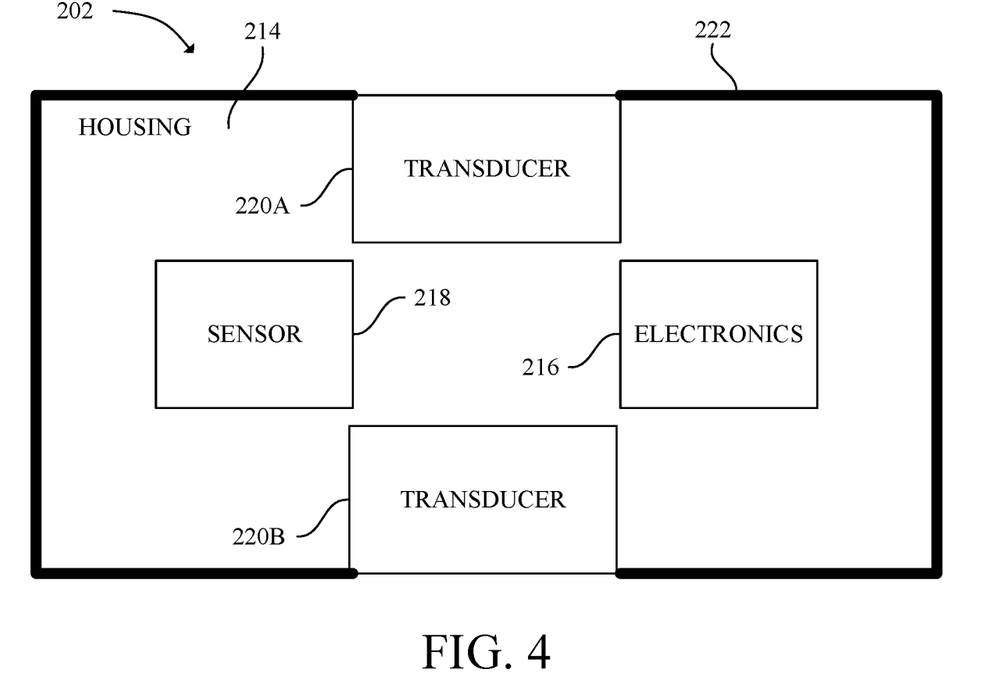
FIG. 4 is a schematic diagram of an ultrasound probe in accordance with an exemplary embodiment.

Referring now to FIG. 3, the communication module 212 is shown in accordance with an exemplary embodiment. As shown in FIG. 3, in some embodiments, the communication module 212 includes a transmit beamformer 224, a transmitter 226, a receiver 228, and a receive beamformer 230. With reference to FIGS. 2-4, when the processor 204 executes computer readable program instructions to begin image acquisition, the processor 204 sends a signal to begin image acquisition to the transmit beamformer 224. The transmit beamformer 224 processes the signal and sends a signal indicative of imaging parameters to the transmitter 226. In response, the transmitter 226 sends a signal to generate ultrasonic waves to the transducer array 220. Elements of the transducer array 220 then generate and output pulsed ultrasonic waves into the body of a patient. The pulsed ultrasonic waves reflect off features within the body (i.e., blood cells, muscular tissue, etc.) thereby producing echoes that return to and are captured by the elements. The elements convert the captured echoes into electrical signals which are sent to the receiver 228. In response, the receiver 228 sends the electrical signals to the receive beamformer 230 which processes the electrical signal into ultrasound image data. The receive beamformer 230 then sends the ultrasound image data to the processor 204. The terms "scan" or "scanning" may be used herein to refer to acquiring data through the process of transmitting and receiving ultrasonic signals.

The processor 204 then further executes computer readable program instructions stored in the system memory 206 to process the ultrasound image data into an image which is output the display 208. The image may be a two-dimensional (2D), three-dimensional (3D) image, or a four-dimensional (4D) ultrasound image. The ultrasound probe 202 may contain all or part of the electronic circuitry to do all or part of the transmit and/or the receive beamforming. For example, all or part of the communication module 212 may be situated within the ultrasound probe 202.

The processor 204 may further execute computer readable program instructions which cause the processor 204 to perform one or more processing operations on the ultrasound data according to a plurality of selectable ultrasound modalities. The ultrasound data may be processed in real-time during a scan as the echo signals are received. As used herein, the term "real-time" includes a procedure that is performed without any intentional delay. For example, the ultrasound probe 202 may acquire ultrasound data at a real-time rate of 7-20 volumes/second. The ultrasound probe 202 may acquire 2D data of one or more planes at a faster rate. It is understood that real-time volume-rate is dependent on the length of time it takes to acquire a volume of data. Accordingly, when acquiring a large volume of data, the real-time volume-rate may be slower.

The ultrasound data may be temporarily stored in a buffer (not shown) during a scan and processed in less than real-time in a live or off-line operation. In one embodiment, wherein the processor 204 includes a first processor 204 and a second processor 204, the first processor 204 may execute computer readable program instructions that cause the first processor 204 to demodulate radio frequency (RF) data and the second processor 204, simultaneously, may execute computer readable program instructions that cause the second processor 204 to further process the ultrasound data prior to displaying an image.

The ultrasound probe 202 may continuously acquire data at, for example, a volume-rate of 10-30 hertz (Hz). Images generated from the ultrasound data may be refreshed at a similar fame-rate. Other embodiments may acquire and display data at different rates (i.e., greater than 30 Hz or less than 10 Hz) depending on the size of the volume and the intended application. In one embodiment, system memory 206 stores at least several seconds of volumes of ultrasound data. The volumes are stored in a manner to facilitate retrieval thereof according to order or time of acquisition.

In various embodiments, the processor 204 may execute various computer readable program instructions to process the ultrasound data by other different mode-related modules (i.e., B-mode, Color Doppler, M-Mode, Color M-mode, spectral Doppler, Elastography, TVI, strain, strain rate, etc.) to form 2D or 3D ultrasound data. For example, one or more modules may generate B-mode, color Doppler, M-mode, spectral Doppler, Elastography, TVI, strain rate, strain, etc. Image lines and/or volumes are stored in the system memory 206 with timing information indicating a time at which the data was acquired. The modules may include, for example, a scan conversion mode to perform scan conversion operations to convert the image volumes from beam space coordinates to display space coordinates. A video processor module may read the image volumes stored in the system memory 206 and cause the processor 204 to generate and output an image to the display 208 in real-time while a scan is being carried out.

While FIG. 2 depicts the processor 204, the system memory 206, the display 208, and the external devices 210 as separate from the ultrasound probe 202, in some embodiments one or more of the processor 204, the system memory 206, the display 208, and the external devices 210 may be in a same device as the ultrasound probe 202. In various embodiments, the ultrasound probe 202 may be a handheld ultrasound probe 202 and the processor 204, the system memory 206, the display 208, and the external devices 210 may be in a separate handheld device.

Figure 5:
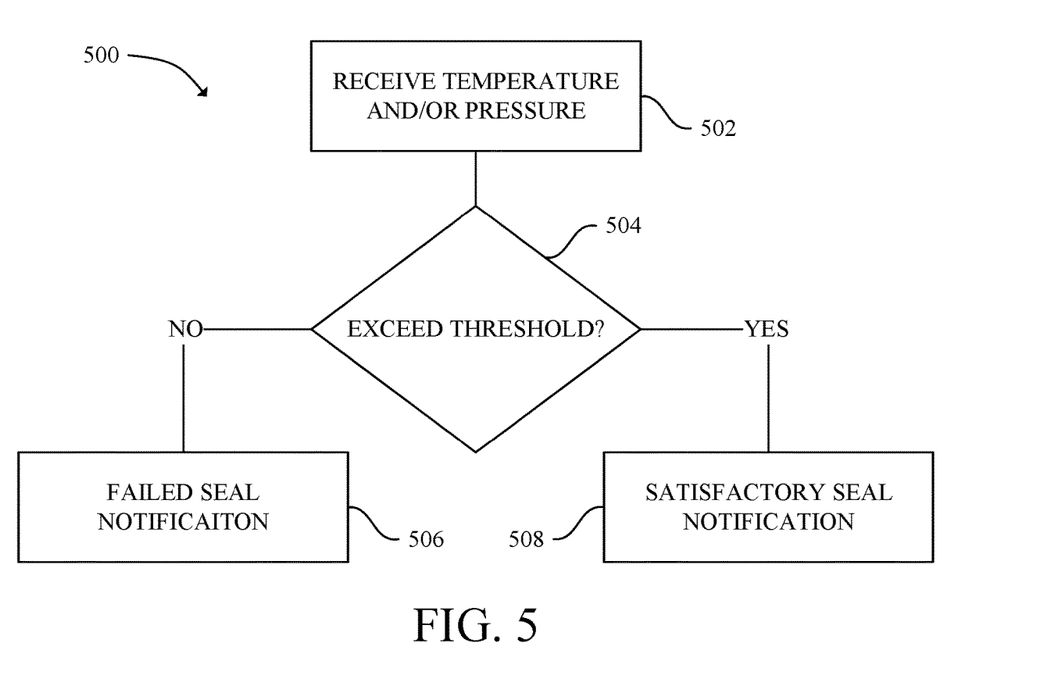
FIG. 5 is a flow chart of a method for actively detecting an ingress of a medical probe in accordance with an exemplary embodiment.
Figure 6:
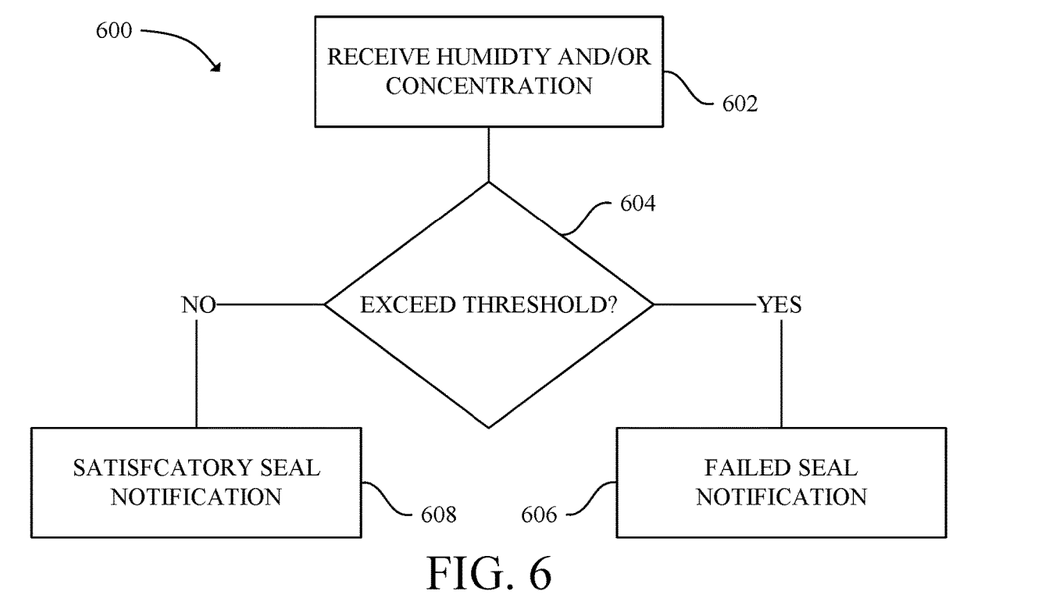
FIG. 6 is a flow chart of another method for actively detecting an ingress of a medical probe in accordance with an exemplary embodiment.

Referring now to FIG. 5, a flow chart of a method 500 for actively detecting an ingress of a medical probe is shown in accordance with an exemplary embodiment. Various aspects of the method 500 may be carried out by a "configured processor." As used herein a configured processor is a processor that is configured according to an aspect of the present disclosure. A configured processor(s) may be the processor 104 or the processor 204. A configured processor executes various computer readable program instructions to perform the steps of the method 500 and the method 600 (FIG. 6). The computer readable program instructions that, when executed by a configured processor, cause a configured processor to carry out the steps of the method 500 and the method 600 may be stored in the system memory 106 or the system memory 206. The technical effect of the method 500 is to determine when a seal of the medical probe 102 or the ultrasound probe 202 has failed.

At 502, the configured processor receives at least one of a detected temperature or a detected pressure from the medical probe 102 or the ultrasound probe 202 as previously discussed herein.

At 504, the configured processor determines whether at least one of the received temperature or pressure exceeds a corresponding temperature or pressure threshold. In some embodiments, the temperature and pressure threshold may be determined as a function of a time the medical probe 102/ultrasound probe 202 has been on as the longer the medical probe 102/ultrasound probe 202 is on, the more heat the medical probe 102/ultrasound probe 202 generates. If properly sealed, an increase in temperature within the medical probe 102/ultrasound probe 202 will cause an increase in pressure. The rise in temperature (and therefore pressure) as a function of time the medical probe 102/ultrasound probe 202 has been on is a generally linear function. In one example, the threshold may be approximately 25° C. when the ultrasound probe 202 has been on for 10 minutes. In another example, the threshold may be 42° C. when the ultrasound probe 202 has been on for 35 minutes. In yet another example, the threshold may be 101300 Pa when the ultrasound probe 202 has been on for 10 minutes. In yet another example, the threshold may be 108100 Pa when the ultrasound probe 202 has been on for 35 minutes.

At 506, in response to determining that at least one of the received temperature or pressure does not exceed the corresponding temperature or pressure threshold, the configured processor determines the seal 118 or the seal 222 has failed. The configured processor determines the seal 118/the seal 222 has failed when the temperature or pressure does not exceed the threshold as the temperature or pressure should exceed the threshold when the medical probe 102/ultrasound probe 202 is properly sealed. When the seal 118/seal 222 fails, heat may exit the medical probe 102/ultrasound probe 202 causing the internal temperature and pressure to fall below an expected temperature and pressure. In response to determining the seal 118/seal 222 has failed, the configured processor generates a notification that indicates the seal 118/seal 222 has failed and outputs the notification. In some embodiments, the notification is a visual notification (i.e., text, color, etc.). In these embodiments, the configured processor outputs the notification to the display 108 or the display 208. In one example, the notification may include text that indicates the seal 108/seal 222 has failed. In another example, the notification may include the color red thereby indicating that the seal 118/seal 222 has failed. In other embodiments, the notification may include audio that indicates that the seal 118/seal 222 has failed.

At 508, in response to determining that at least one of the temperature or pressure exceeds the corresponding temperature or pressure threshold, the configured processor determines the seal 118/seal 222 has not failed, generates a notification that indicates the seal 118/seal 222 is satisfactory, and outputs the notification. In some embodiments, the notification is a visual notification. In these embodiments, the configured processor outputs the notification to the display 108/display 208. In one example, the notification may include text that indicates the seal 118/seal 222 has not failed. In another example, the notification may include the color green thereby indicating that the seal 118/seal 222 has not failed. In other embodiments, the notification may include audio that indicates that the seal has not failed.

Referring now to FIG. 6, a flow chart of a method 600 for actively detecting an ingress of a medical probe is shown in accordance with an exemplary embodiment. Various aspects of the method 600 may be carried out by a configured process. The technical effect of the method 600 is to determine when a seal of the medical probe 102 or the ultrasound probe 202 has failed.

At 602, the configured processor receives at least one of a detected humidity or a detected concentration of a gas from the medical probe 102 or the ultrasound probe 202 as previously discussed herein.

At 604, the configured processor determines whether at least one of the received humidity or concentration of a gas exceeds a corresponding humidity or concentration threshold. The humidity and concentration threshold may be determined as a function of an expected humidity or concentration of a gas within the medical probe 102/ultrasound probe 202. In one example the threshold may be 5% relative humidity (RH), in another example, the threshold may be 20% RH. In yet another example, the threshold may be 5 ppm. In yet another example, the threshold may be 15 ppm.

At 606, in response to determining that at least one of the received humidity or concentration exceeds the corresponding humidity or concentration threshold, the configured processor determines the seal 118/seal 222 has failed, generates a notification that indicates the seal 118/seal 222 has failed, and outputs the notification. The configured processor determines the seal 118/seal 222 has failed when the humidity or concentration of a gas exceeds the threshold as when the seal 118/seal 222 fails, water or a cleaning solution may enter the medical probe 102/ultrasound probe 202. When the medical probe 102/ultrasound probe 202 generates heat, water or a cleaning solution that has entered the medical probe 102/ultrasound probe 202 may evaporate causing the internal humidity or concentration of a gas to exceed an expected humidity or concentration. In some embodiments, the notification is a visual notification. In these embodiments, the configured processor outputs the notification to the display 108/display 208. In one example, the notification may include text that indicates the seal 118/seal 222 has failed. In another example, the notification may include the color red thereby indicating that the seal 118/seal 222 has failed. In other embodiments, the notification may include audio that indicates the seal 118/seal 222 has failed.

At 608, in response to determining that at least one of the humidity or concentration of a gas does not exceed the corresponding humidity or concentration threshold, the configured processor determines the seal 118/seal 222 has not failed generates a notification that indicates the seal 118/seal 222 is satisfactory, and outputs the notification. In some embodiments, the notification is a visual notification. In these embodiments, the configured processor outputs the notification to the display 108/display 208. In one example, the notification may include text that indicates the seal 118/seal 222 has not failed. In another example, the notification may include the color green thereby indicating that the seal 118/seal 222 has not failed. In other embodiments, the notification may include audio that indicates that the seal 118/seal 222 has not failed.

Thus, while the information has been described above with particularity and detail in connection with what is presently deemed to be the most practical and preferred aspects, it will be apparent to those of ordinary skill in the art that numerous modifications, including, but not limited to, form, function, manner of operation, and use may be made without departing from the principles and concepts set forth herein. Also, as used herein, the examples and embodiments are meant to be illustrative only and should not be construed to be limiting in any manner.

What is claimed is:

1. A method comprising:
   monitoring, with a sensor within an ultrasound probe, an internal environment of the medical probe;
   detecting, with the sensor, at least one of a temperature, humidity, or concentration of a gas within the medical probe;
   determining, with a processor, that at least one of the temperature, humidity, or the concentration of the gas is above or below a threshold; and
   outputting, with the processor, a notification in response to determining that at least one of the temperature, humidity, or the concentration of gas is above or below the threshold,
   wherein the threshold corresponds to a temperature and the method further comprises:
   determining, with the processor, the threshold as a function of a time the ultrasound probe has been on; and
   wherein said determining with the processor that at least one of the temperature, humidity, or the concentration of the gas is above or below a threshold comprises determining that the temperature is below the threshold.

2. The method of claim 1, wherein the notification is output to a display.

3. The method of claim 1, wherein a second threshold corresponds to a humidity and wherein said determining with the processor that at least one of the temperature, humidity, or the concentration of the gas is above or below a threshold further comprises determining the humidity is above the second threshold.

4. The method of claim 1, wherein a second threshold corresponds to a concentration of a gas and wherein said determining with the processor that at least one of the temperature, humidity, or the concentration of the gas is above or below a threshold further comprises determining the concentration of the gas is above the second threshold.

5. The method of claim 4, wherein the gas is one of ethane, isoprene, ethanol, acetone, or carbon monoxide.

6. A system comprising:
   an ultrasound probe;
   a sensor within the medical probe;
   a processor in communication with the sensor; and
   a computer readable storage medium in communication with the processor, wherein the processor executes program instructions stored in the computer readable storage medium which cause the processor to:
   receive at least one of a temperature, humidity, or concentration of a gas from the sensor;
   determine whether at least one of the temperature, humidity, or concentration of a gas is above or below a threshold;
   generate a notification in response to determining whether the at least one of the temperature, humidity, or concentration of the gas is above or below the threshold; and
   output the notification,
   wherein the threshold corresponds to a temperature and the instructions further cause the processor to:
   determine the threshold as a function of a time the ultrasound probe has been on; and
   wherein said determining that at least one of the temperature, humidity, or the concentration of the gas is above or below a threshold comprises determining that the temperature is below the threshold.

7. The system of claim 6, wherein the notification indicates a seal that hermetically seals the medical probe has failed and the system further comprises:
   a handheld device with a display and the processor, and the instructions further cause the processor to:
   output the notification to the display.

8. The system of claim 7, wherein
   a second threshold corresponds to a humidity and the instructions further cause the processor to:
   generate the notification in response to determining the humidity is above the second threshold.

9. The system of claim 7, wherein
   a second threshold corresponds to a concentration of a gas and the instructions further cause the processor to:
   generate the notification in response to determining the concentration of the gas is above the second threshold.

\* \* \* \* \*